(12) United States Patent
Tanaka et al.

(10) Patent No.: US 9,625,319 B2
(45) Date of Patent: Apr. 18, 2017

(54) CHIP FOR PLASMA GENERATION, PLASMA GENERATOR, AND PLASMA SPECTROMETRY METHOD

(71) Applicant: ARKRAY, Inc., Kyoto (JP)

(72) Inventors: Takashige Tanaka, Kyoto (JP); Yasunori Shiraki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 231 days.

(21) Appl. No.: 14/632,107

(22) Filed: Feb. 26, 2015

(65) Prior Publication Data
US 2015/0247757 A1    Sep. 3, 2015

(30) Foreign Application Priority Data

Feb. 28, 2014  (JP) ................. 2014-039506
Feb. 24, 2015  (JP) ................. 2015-033833

(51) Int. Cl.
| | | |
|---|---|---|
| *G01J 3/30* | (2006.01) |
| *G01J 3/443* | (2006.01) |
| *G01N 21/67* | (2006.01) |
| *H05H 1/48* | (2006.01) |
| *B23K 10/00* | (2006.01) |
| *G01J 3/12* | (2006.01) |
| *H05H 1/46* | (2006.01) |

(52) U.S. Cl.
CPC .......... *G01J 3/443* (2013.01); *B23K 10/006* (2013.01); *G01J 3/12* (2013.01); *G01N 21/67* (2013.01); *H05H 1/46* (2013.01); *H05H 1/48* (2013.01)

(58) Field of Classification Search
CPC .......... G01J 3/443; G01N 21/67–21/69; H05H 1/46; H05H 2001/469–2001/4697; H05H 1/48
See application file for complete search history.

(56) References Cited

U.S. PATENT DOCUMENTS

| | | | | |
|---|---|---|---|---|
| 3,809,479 A | * | 5/1974 | Whelan ................ | G01N 21/67 250/307 |
| 3,811,841 A | * | 5/1974 | Kassel ................ | G01N 35/08 324/71.4 |

(Continued)

FOREIGN PATENT DOCUMENTS

| | | |
|---|---|---|
| EP | 1734360 A1 | 12/2006 |
| EP | 1734360 B1 | 5/2014 |

(Continued)

OTHER PUBLICATIONS

Extended European Search Report issued in corresponding European Patent Application No. 15157054.6 dated Jul. 13, 2015.

*Primary Examiner* — Kara E Geisel
*Assistant Examiner* — Rufus Phillips
(74) *Attorney, Agent, or Firm* — Morgan, Lewis & Bockius LLP

(57) ABSTRACT

A chip for plasma generation, a plasma generator, and a plasma spectrometry method are described, having high reproducibility of plasma light emission without a requirement of a discharge unit for removing air bubbles, wherein the chip includes a channel comprising a first region, a narrow portion, and a second region, where the narrow portion is in communication with the first region and the second region and has a cross-sectional area smaller than the first region and the second region.

14 Claims, 5 Drawing Sheets

(56) References Cited

U.S. PATENT DOCUMENTS

| | | | | |
|---|---|---|---|---|
| 4,250,433 | A * | 2/1981 | Bernard | G01N 21/67 |
| | | | | 313/231.71 |
| 4,641,968 | A * | 2/1987 | Grandy | G01N 21/67 |
| | | | | 315/209 CD |
| 5,184,016 | A * | 2/1993 | Ronan | G01N 21/67 |
| | | | | 250/288 |
| 5,241,243 | A * | 8/1993 | Cirri | H05H 1/48 |
| | | | | 313/231.31 |
| 5,408,315 | A * | 4/1995 | Mitchell | H01J 49/105 |
| | | | | 356/311 |
| 5,565,114 | A * | 10/1996 | Saito | G01N 21/68 |
| | | | | 156/345.25 |
| 5,728,253 | A * | 3/1998 | Saito | B81C 1/00587 |
| | | | | 118/712 |
| 7,011,791 | B2 * | 3/2006 | Weigl | B01F 5/0646 |
| | | | | 422/417 |
| 7,417,730 | B2 * | 8/2008 | Duan | G01J 3/443 |
| | | | | 356/316 |
| 7,704,294 | B2 * | 4/2010 | Ariessohn | G01N 1/2202 |
| | | | | 209/143 |
| 7,875,825 | B2 | 1/2011 | Takamura et al. | |
| 9,222,890 | B2 * | 12/2015 | Kohara | G01N 21/69 |
| 2007/0164003 | A1 | 7/2007 | Takamura et al. | |
| 2010/0277724 | A1 * | 11/2010 | Bounouar | G01N 21/66 |
| | | | | 356/316 |
| 2013/0252234 | A1 * | 9/2013 | Nassef | B01L 3/502707 |
| | | | | 435/5 |
| 2013/0321803 | A1 | 12/2013 | Kohara et al. | |

FOREIGN PATENT DOCUMENTS

| | | |
|---|---|---|
| JP | 2004-069430 A | 3/2004 |
| JP | 3932368 B2 | 6/2007 |
| JP | 2011-180045 A | 9/2011 |
| JP | 2012-185064 A | 9/2012 |

* cited by examiner

CHIP FOR PLASMA GENERATION, PLASMA GENERATOR, AND PLASMA SPECTROMETRY METHOD

TECHNICAL FIELD

The present invention relates to a chip for plasma generation, a plasma generator, and a plasma spectrometry method.

BACKGROUND

The patent literature discloses a plasma generator as an element analyzer. The plasma generator is a device in which air bubbles are generated in a channel that includes a narrow portion, plasma is generated in the air bubbles, and the resulting light emission is measured. In patent literature 1, plasma in the narrow portion of the channel is measured, and in patent literature 2, plasma in a region other than the narrow portion is measured. However, in each of the described devices, there is a problem because the retention of generated air bubbles in the narrow portion of the channel exerts an influence on the intensity of the plasma light emission, which results in low reproducibility of the plasma light emission.

In order to solve this problem, patent literature 3 discloses a method for avoiding the retention of air bubbles by removing the air bubbles through moving a solution in the channel. However, there is a problem in that a discharge unit such as a syringe pump is required in order to move the solution, with the result that the size of the plasma generator is increased.

CITATION LIST

Patent Literature

Patent Literature 1: Japanese Patent No. 3932368
Patent Literature 2: JP 2012-185064 A
Patent Literature 3: JP 2011-180045 A

SUMMARY OF INVENTION

Technical Problem

The present invention is intended to provide a chip for plasma generation, a plasma generator, and a plasma spectrometry method, having high reproducibility of plasma light emission without the requirement of a discharge unit for removing air bubbles, for example.

Solution to Problem

In order to achieve the aforementioned objectives, the chip for plasma generation of the present invention includes: a channel, where the channel has a first region, a narrow portion, and a second region, where the narrow portion is in communication with the first region and the second region and has a cross-sectional area smaller than the first region and the second region, and the chip satisfies at least one of the following conditions (1) and (2): (1) at least one of the inner walls of the first region and the second region has a grooved portion; (2) the chip includes a cathode fixed to the inner wall of the first region.

The plasma generator of the present invention comprises the chip for plasma generation of the present invention.

The plasma spectrometry method of the present invention comprises: an electric field generation step of generating an electric field in a channel containing a conductive solution supplied therein; and a detection step of detecting plasma light emission generated in the channel by the generation of the electric field, where the channel has a first region, a narrow portion, and a second region, and wherein the narrow portion is in communication with the first region and the second region and has a cross-sectional area smaller than the first region and the second region, and the plasma spectrometry method satisfies at least one of the conditions (1) and (2): (1) at least one of the inner walls of the first region and the second region has a grooved portion, and an anode and a cathode are arranged so that the narrow portion is positioned between the anode and the cathode; and (2) the anode and the cathode are arranged so that the narrow portion is positioned between the anode and the cathode, and the cathode is fixed to the inner wall of the first region.

Advantageous Effects of the Invention

As a result of the studies conducted by the inventors of the present invention, the inventors observed the following facts and achieved the present invention. The present invention, however, is not limited by the description herein. The inventors observed the following facts regarding low reproducibility in a conventional plasma generator. That is, plasma is generated at an interface between the gas (air bubbles) and the liquid (conductive solution) (hereinafter referred to as a "gas-liquid interface"), and therefore, formation of the gas-liquid interface between electrodes is important. However, in the conventional plasma generator, because of the retention of air bubbles generated in the channel, it is difficult to maintain constant formation of the gas-liquid interface in the channel. Accordingly, the liquid resistance value between electrodes varies, and the voltage to be applied to the channel becomes unstable. Thus, the reproducibility of the plasma light emission is decreased. Hence, the inventors enabled the influence of the change in the liquid resistance value between electrodes to be avoided, the voltage to be applied to the channel to be stabilized, and the position of the gas-liquid interface to be controlled by forming a grooved portion in at least one of the inner walls of the first region and the second region as shown in the condition (1) or by fixing a cathode to the inner wall of the first region as shown in the condition (2). Specifically, the inventors enabled the gas-liquid interface to be formed and present in the narrow portion of the channel. As a result, the inventors achieved high reproducibility of plasma light emission in the present invention.

According to the chip for plasma generation of the present invention, superior reproducibility of plasma light emission can be achieved without using a discharge unit for removing air bubbles. Therefore, the present invention is useful in elemental analysis utilizing plasma generation.

BRIEF DESCRIPTION OF DRAWINGS

FIG. 1A is a top view. FIG. 1B is a cross-sectional view in the I-I direction of FIG. 1A. FIG. 1C is a cross-sectional view in the II-II direction of FIG. 1B. FIG. 1D is an enlarged view of a region (X) indicated by dashed lines of FIG. 1B. FIG. 1E is a cross-sectional view in the III-III direction of FIG. 1B.

DESCRIPTION OF EMBODIMENTS

Figure 1A:
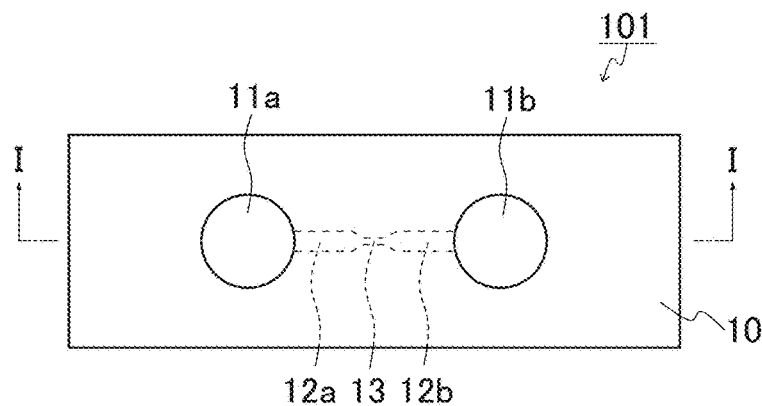
FIGS. 1A to 1E are schematic views showing an example of a first chip for plasma generation according to the present invention.

Each of the chips for plasma generation, the plasma generator, and the plasma spectrometry method of the present invention encompasses the first embodiment in which at least one of the inner walls of the first region and the second region has a grooved portion and the second embodiment in which the cathode is fixed to the inner wall of the first region. The first embodiment and the second embodiment are described below. The first embodiment can be described with reference to the description of the second embodiment, the second embodiment can be described with reference to the description of the first embodiment, and the present invention may be an embodiment satisfying both of the first embodiment and the second embodiment, unless otherwise shown.

1. First Embodiment of the Present Invention (1) Chip for Plasma Generation

As mentioned above, the first chip for plasma generation of the present invention comprises a channel. The channel has a first region, a narrow portion, and a second region. The narrow portion is in communication with the first region and the second region and has a cross-sectional area smaller than the first region and the second region. The chip satisfies the following condition (1): (1) at least one of the inner walls of the first region and the second region has a grooved portion.

The first chip for plasma generation of the present invention enables high reproducibility of plasma light emission by having a grooved portion in at least one of the inner walls of the first region and the second region. As mentioned above, in the chip for plasma generation of the present invention, at least one of the inner walls of the first region and the second region in the channel has a grooved portion. Therefore, even if air bubbles are retained in the channel, a conductive liquid is present in the grooved portion. It is assumed that by the presence of the conductive liquid in the grooved portion, variations in liquid resistance values between electrodes are suppressed, and voltage to be applied to the channel is stabilized, and thus, the formation of the gas-liquid interface can be maintained to be constant. The present invention, however, is not limited by this assumption.

In the first chip for plasma generation of the present invention, for example, only the inner wall of the first region may have the grooved portion, only the inner wall of the second region may have the grooved portion, or both of the inner walls of the first region and the second region may have the grooved portions.

In the chip for plasma generation of the present invention, as mentioned above, the channel has a first region, a narrow portion, and a second region, and each of these has a void (hollow), so that the inside of the regions are in communication with each other in this order. In the chip for plasma generation of the present invention, the direction from the first region toward the second region is referred to as the "longitudinal direction", the "axis direction", or the "electric field direction"; the first region side is referred to as the upstream side; and the second region side is referred to as the downstream side with a central focus on the narrow portion. The direction that is perpendicular to the longitudinal direction and is the plane direction is referred to as the "width direction", and the direction that is perpendicular to the longitudinal direction and is the vertical direction of the chip is referred to as the "height direction" or "depth direction". The distance in the longitudinal direction is referred to as the "length", the distance in the width direction is referred to as the "width", and the distance in the height direction is referred to as the "height". The "cross-sectional area" in the channel means a cross-sectional area of the void inside the channel in the width direction (direction perpendicular to the longitudinal direction), unless otherwise shown.

The shape of the channel is not particularly limited, and examples of the cross-sectional shape of the channel include: circular shapes such as a circle, an exact circle, and an ellipse; a semicircular shape; and polygonal shapes such as a triangle, a quadrangle, a square, and a rectangle. In the channel, the cross-sectional shapes of the first region, the narrow portion, and the second region may be different from each other, for example.

In the chip for plasma generation of the present invention, the narrow portion is a region having a cross-sectional area smaller than the first region and the second region and is preferably a region having a cross-sectional area significantly smaller than the first region and the second region. It is preferred that the narrow portion is a region with a central focus on a portion having the smallest cross-sectional area in the channel. It is preferred that the narrow portion has an almost constant cross-sectional area over the full length thereof. "The narrow portion having an almost constant cross-sectional area" also encompasses the meaning of a region having a cross-sectional area gradually increased from the upstream side toward the downstream side in the longitudinal direction with a central focus on a portion having the smallest cross-sectional area in addition to the meaning of a region having a completely constant cross-sectional area, for example. The cross-sectional area may be successively or non-successively increased, for example. In this case, the narrow portion is a successive region having a cross-sectional areas of 50,000 times or less, 1000 times or less, 500 times or less, or 100 times or less relative to the smallest cross-sectional area as 1, for example.

The cross-sectional area of the narrow portion may be set by narrowing the width, reducing the height, or both of them, relative to the first region and the second region.

In the chip for plasma generation of the present invention, the shape of the first region is not particularly limited as long as it has a cross-sectional area larger than the narrow portion.

The first region may have an almost constant cross-sectional area or different cross-sectional areas over the full length thereof, for example.

In the former case, "having an almost constant cross-sectional area" encompasses the meaning of a region having a cross-sectional area gradually increased from the end on the downstream side (end on the narrow portion side) toward the end on the upstream side in the longitudinal direction in addition to a region having a completely constant cross-sectional area, for example. The cross-sectional area may be successively or non-successively increased, for example. In this case, the first region is a successive region having cross-sectional areas of 5000 times or less, 1000 times or less, or 500 times or less, relative to an average cross-sectional area over the full length as 1, for example. In this case, it can also be said that the cross-sectional area at the interface between the narrow portion and the first region in the channel changes at an angle of about 90° to at least one of the longitudinal direction, the width direction, and the height direction, for example.

In the latter case, the form of the first region can be, for example, a form in which the cross-sectional area is successively or non-successively increased from the end on the downstream side toward the end on the upstream side in the longitudinal direction, i.e., a form in which the cross-sectional area of the first region is gradually increased over the full length. The variations in cross-sectional area may be set by the variations of width, height, or both of them. In this case, the form of the first region may be a form of a tapered portion in which one or both of the width and the height is enlarged from the end on the downstream side toward the end on the upstream side so as to have a tapered shape, for example.

In the latter case, the form of the first region may be a form in which the cross-sectional area is successively or non-successively increased from the end on the downstream side toward a predetermined portion on the upstream side in the longitudinal direction and is almost constant from the predetermined portion toward the end on the upstream side, for example. The variations in cross-sectional area may be set by the variations in width or height. In this case, the form of the first region may be a form having: a tapered portion in which one or both of the width and the height is enlarged from the end on the downstream side toward the predetermined portion so as to have a tapered shape; and a non-tapered portion in which one or both of the width and the height is constant from the predetermined portion toward the end on the upstream side.

In the case where the first region has a tapered portion in which the height is enlarged from the downstream side toward the upstream side so as to have a tapered shape, the enlarged angle of the tapered portion is, for example, from 10° to 90°, from 10° to 80°, from 10° to 45° to the longitudinal direction. In the case where the first region has a tapered portion in which the width is enlarged from the downstream side toward the upstream side so as to have a tapered shape, the enlarged angle of the tapered portion is, for example, from 10° to 90°, from 10° to 80°, from 10° to 45° to the longitudinal direction.

In the chip for plasma generation of the present invention, the shape of the second region is not particularly limited as long as it is a region having a cross-sectional area larger than the narrow portion. The second region can be described with reference to the description of the first region by reading the "first region" as the "second region", "upstream" as "downstream", and "downstream" as "upstream". The shapes of the first region and the second region may be symmetrical to each other, and the first region and the second region may be under the same conditions or different conditions, or the shapes of the first region and the second region may be asymmetrical to each other.

The cross-sectional areas of the first region and the second region are, for example, more than 1×, 3× or more, 10× or more, 30× or more, or 100× or more relative to the smallest cross-sectional area in the narrow portion. The upper limit thereof is not particularly limited and is, for example, 10,000 times or less, 8000 times or less, or 5000 times or less.

In the chip for plasma generation of the present invention, the width and the height of each portion are not particularly limited. The length of the narrow portion is, for example, from 1/1 to 1/10,000, from 1/1 to 1/1000, or from 1/10 to 1/100 relative to the length of the channel, i.e., the length from the end on the upstream side of the first region to the end on the downstream side of the second region.

The length from the end on the upstream side of the first region to the end on the downstream side of the second region is, for example, from 1 to 50 mm, from 1 to 10 mm, or from 3 to 7 mm, and the length of the narrow portion is, for example, from 1 to 1000 μm, from 1 to 600 μm, or from 1 to 400 μm.

As to the first region and the second region, the width is, for example, from 2 μm to 30 mm, from 300 μm to 5 mm, or from 500 μm to 1 mm, and the height is, for example, from 0.5 μm to 1 mm, from 10 to 300 μm, or from 50 to 200 μm. As to the narrow portion, the width is, for example, from 0.5 μm to 1 mm, from 10 to 300 μm, or from 50 to 200 μm, and the height is, for example, from 0.5 μm to 1 mm, from 10 to 300 μm, or from 50 to 200 μm.

In the first chip for plasma generation, a portion in which the grooved portion is formed is not limited as long as it is at least one of the inner walls of the first region and the second region, for example. The grooved portion can also be referred to as a concave portion in the inner wall of the first region or the second region. In the first chip for plasma generation, it is preferred that the inner wall of the first region or the second region has a grooved portion along the longitudinal direction, for example. The grooved portion may be formed in the inner wall of any of the upper surface, the lower surface, and the side surface of the first region or the second region and may be formed in one place or multiple places.

The length of the grooved portion is not particularly limited, and the grooved portion may be formed in the first region over the full length or in a part of the first region, for example. The size of the grooved portion is not particularly limited and is, for example, preferably a size capable of holding a conductive solution and not causing air bubbles generated by applying a voltage to enter. In the case where the first region has a grooved portion, the grooved portion is, for example, preferably formed in a position near the end on the first region side of the narrow portion. In the case where the second region has a grooved portion, the grooved portion is, for example, preferably formed in a position near the end on the second region side of the narrow portion.

As a specific example, in the case where the first region has the grooved portion, the conditions of the grooved portion are as follows, for example. The distance from the end on the upstream side of the narrow portion (the end on the first region side) to the end on the downstream side of the grooved portion (the end on the narrow portion side) in the longitudinal direction is, for example, from 0 to 50 mm, from 1 to 10 mm, or from 3 to 7 mm. The depth of the grooved portion is, for example, from 0.1 to 10 mm, from 0.1 to 5 mm, or from 0.5 to 1 mm, the width of the grooved portion is, for example, from 0 to 10 mm, or from 0 to 1 mm, and the length of the grooved portion is, for example, from 0 to 50 mm, or from 0 to 5 mm.

As a specific example, in the case where the second region has the grooved portion, the conditions of the grooved portion are as follows, for example. The distance from the end on the downstream side of the narrow portion (the end on the second region side) to the end on the upstream side of the grooved portion (the end on the narrow portion side) is, for example, from 0 to 50 mm, from 1 to 10 mm, or from 3 to 7 mm. The depth of the grooved portion is, for example, from 0.1 to 10 mm, from 0.1 to 5 mm, or from 0.5 to 1 mm, and the width of the grooved portion is, for example, from 0 to 10 mm, or from 0 to 1 mm, and the length of the grooved portion is, for example, from 0 to 50 mm, or from 0 to 5 mm.

The shape of the grooved portion is not particularly limited, and examples of the cross section of the grooved portion in the width direction includes: circular shapes such as a circle, an exact circle, and an ellipse; a semicircular shape; and polygonal shapes such as a triangle, a quadrangle, a square, and a rectangle.

In the chip for plasma generation of the present invention, the chip itself may include an electrode, or a device in which the chip is set may include an electrode, for example. In the chip for plasma generation of the present invention, a pair of electrodes, i.e., a cathode and an anode may be arranged so that the narrow portion is positioned between the cathode and the anode in use, for example. Specifically, for example, the chip itself may include a pair of electrodes (electrode system) including an anode and a cathode; the chip itself may include a cathode, and a device in which the chip is set may include an anode; or the chip itself may include an anode, and a device in which the chip is set may include a cathode. In the case where the device includes an electrode, the electrode is, for example, preferably a solid electrode in which the chip can be inserted and can be a bar electrode or the like as a specific example.

In the chip for plasma generation of the present invention, a cathode is preferably arranged on the upstream side with a central focus on the narrow portion, more preferably arranged in the first region. In the case where the first region has a grooved portion, the cathode is preferably arranged in the grooved portion of the first region.

In the case where the chip itself includes a cathode, the cathode is preferably fixed to the inner wall of the first region, more preferably fixed to the inner wall of the grooved portion in the first region. In the case where the cathode is fixed to the inner wall of the grooved portion in the first region, a concave portion is formed in another inner wall of the first region even through the grooved portion has the electrode. By fixing the cathode to the inner wall of the first region, further superior reproducibility of plasma light emission can be achieved as described in the second embodiment described below, for example.

In the case where the cathode is a fixed electrode, the cathode may be an electrode formed by coating the inner wall of the first region with a conductive material or an electrode formed by burying a conductive material in the inner wall of the first region, for example.

In the first region, a portion to which the cathode is fixed (hereinafter also referred to as a cathode fixation portion) is not particularly limited, and it is preferred that the end on the downstream side of the cathode fixation portion (end on the narrow portion side) is near the narrow portion. The distance between the end on the downstream side of the cathode fixation portion in the first region and the end on the upstream side of the narrow portion (end on the first region side) is as described below, for example. The lower limit of the distance in the longitudinal direction is, for example, 0 mm or more, or 0.5 mm or more, the upper limit of the same is, for example, 5 mm or less, 3 mm or less, 2 mm or less, or 1 mm or less, and the range of the same is, for example, from 0 to 5 mm, from 0 to 3 mm, from 0 to 2 mm, from 0 to 1 mm, and from 0.5 to 5 mm, from 0.5 to 3 mm, from 0.5 to 2 mm, or from 0.5 to 1 mm. The end on the upstream side of the cathode fixation portion is not particularly limited and may be, for example, the end on the upstream side of the first region. The cathode may be, for example, fixed to the entire inner wall of the first region.

In the chip for plasma generation of the present invention, the anode is preferably arranged on the downstream side with a central focus on the narrow portion, more preferably arranged in the second region. In the case where the chip itself includes an anode, the anode is, for example, preferably fixed to the inner wall of the second region. In the case where the second region has a grooved portion, the anode may be arranged in the grooved portion of the second region, for example. In the second region, the distance between the end on the upstream side of the portion on which the anode is fixed (hereinafter also referred to as an anode fixation portion) and the end on the downstream side of the narrow portion (end on the second region side) is, for example, preferably from 0 mm or more or from 0.2 mm or more in the longitudinal direction.

In the case where the anode is a fixed electrode, as in the cathode, the anode may be an electrode formed by coating the inner wall of the second region with a conductive material or an electrode formed by burying a conductive material in the inner wall of the second region. The anode fixation portion is not particularly limited and can be described with reference to the description of the cathode by reading the "first region" as the "second region", the "upstream side" as "downstream side", "downstream side" to "upstream side", for example.

The material of the electrode is not particularly limited as long as it is a solid conductive material, with examples thereof including platinum, gold, carbon, zinc, brass, copper, stainless steel, iron, and the like. The material of the cathode is, for example, preferably carbon, and the material of the anode is, for example, preferably carbon.

A method for forming an electrode by coating with a conductive material is not particularly limited, and a conventionally known method such as sputtering can be employed.

The chip for plasma generation of the present invention preferably further includes a first reservoir and a second reservoir, for preserving a conductive solution. In this case, for example, one end of the first region is in communication with the narrow portion, the other end of the first region is in communication with the first reservoir, one end of the second region is in communication with the narrow portion, and the other end of the second region is in communication with the second reservoir. In the chip for plasma generation of the present invention, the cathode may be arranged in the first reservoir, for example, and the anode may be arranged in the second reservoir, for example. In this case, as mentioned above, the chip itself may include the electrode, or a device in which the chip is set may include the electrode.

In the case where the cathode and the anode are fixed electrodes such as mentioned above, the cathode may be fixed to the entire inner wall of the first reservoir, and the anode may be fixed to the entire inner wall of the second reservoir, for example.

The shapes and the sizes of the first reservoir and the second reservoir are not particularly limited as long as they can preserve a conductive solution. The shapes of the first reservoir and the second reservoir are not particularly limited, and examples thereof include polygonal prism shapes such as a triangular prism and a quadrangular prism and cylindrical shapes such as an exact cylinder and an elliptic cylinder, and a conical shape.

As a specific example, as to the first reservoir and the second reservoir, the diameter is, for example, from 1 to 10 mm, from 1 to 6 mm, or from 2 to 4 mm, the height is, for example, from 1 to 20 mm, from 1 to 10 mm, or from 1 to 6 mm, and the volume is, for example, from 1 to 1000 µL, from 30 to 150 µL, or from 60 to 110 µL.

The material of the chip for plasma generation of the present invention is not particularly limited, and for example, it is preferred that the inner wall of the chip except for the electrode is formed of the insulating material, and it is more preferred that the entire chip except for the electrode is formed of the insulating material. A method for producing the chip for plasma generation of the present invention is not particularly limited, and for example, a molded article having a channel and the like may be produced by injection molding or the like, or a channel and the like may be formed in a base material such as a plate. A method for forming a channel and the like is not particularly limited, and examples thereof include lithography and cutting.

The insulating material is not particularly limited, and examples thereof include a resin, silicone, glass, paper, ceramics, and rubber. Examples of the resin include thermoplastic resins such as polyethylene, polypropylene, polystyrene, polyvinyl chloride, polyethylene terephthalate, polymethacrylate, polyamide, a saturated polyester resin, and an acrylic resin, epoxy resins such as an urea resin, a melamine resin, a phenol resin, a fluorine resin, and glass epoxy, and a thermosetting resin such as an unsaturated polyester resin. The silicone can be, for example, polydimethylsiloxane.

The application of the chip for plasma generation of the present invention is not particularly limited, and for example, the chip can cause a conductive solution to be supplied to the channel, an electric field to be generated in the channel, or plasma to be generated in channel, for example. By detecting light emission caused by the plasma, a sample contained in the conductive solution can be analyzed, for example. When the analysis is performed using the chip for plasma generation of the present invention as described above, the chip for plasma generation of the present invention can also be referred to as a chip for plasma light emission analysis. It is preferred that the generation of the electric field is performed by applying a voltage to an electrode system, and in addition to this, for example, an electric field may be generated by microwave or the like, for example.

(2) Plasma Generator

A first plasma generator of the present invention includes the first chip for plasma generation of the present invention as mentioned above. The first plasma generator of the present invention is characterized in that it includes the first chip for plasma generation, and the other configurations and conditions are not particularly limited. The first plasma generator of the present invention can be described with reference to the description of the first chip for plasma generation of the present invention, unless otherwise shown.

The plasma generator of the present invention preferably further includes a voltage application unit, for example.

The plasma generator of the present invention can analyze a sample by generating plasma and detecting light emission caused by the plasma, for example. Therefore, the plasma generator of the present invention can also be referred to as a plasma spectrophotometer, for example.

The plasma generator of the present invention preferably further includes a detection unit that detects plasma light emission generated in the chip for plasma generation, for example. The detection unit may be an unit that detects plasma light emission generated in the narrow portion of the channel in the chip for plasma generation of the present invention or generated in a portion other than the narrow portion, for example.

A region to be detected by the detection unit is not particularly limited and may be, for example, only the narrow portion, a region including the narrow portion (a region including both of the narrow portion and another portion), or a region other than the narrow portion in the chip for plasma generation of the present invention. The center of the region to be detected is not particularly limited, and for example, in the chip for plasma generation of the present invention, the center of the narrow portion or a portion moved from the center of the narrow portion toward the upstream side or the downstream side in the longitudinal direction may be set as the central point. As a specific example, for example, the region to be detected is preferably only the narrow portion with the center of the narrow portion as the central point or a portion other than the narrow portion with a point other than the center of the narrow portion as the central point.

(3) Plasma Spectrometry Method

As mentioned above, the first plasma spectrometry method of the present invention includes: an electric field generation step of generating an electric field in a channel containing a conductive solution supplied therein; and a detection step of detecting plasma light emission generated in the channel by the generation of the electric field, the channel has a first region, a narrow portion, and a second region, the narrow portion is in communication with the first region and the second region and has a cross-sectional area smaller than the first region and the second region, and the plasma spectrometry method satisfies the condition (1): (1) at least one of the inner walls of the first region and the second region has a grooved portion, and an anode and a cathode are arranged so that the narrow portion is positioned between the anode and the cathode.

In the plasma spectrometry method of the present invention, the first chip for plasma generation or the first plasma generator of the present invention can be used, for example. The plasma spectrometry method of the present invention can be described with reference to the descriptions of the chip for plasma generation and the plasma generator of the present invention, unless otherwise shown. It is preferred that the generation of electric field is performed by applying a voltage to an electrode system, and in addition to this, for example, an electric field may be generated by microwave or the like, for example.

The plasma spectrometry method of the present invention may further include a conductive solution supplying step of supplying a conductive solution to a channel. The conductive solution can be, for example, a liquid sample and may further contain an electrolyte for imparting conductivity. Examples of the electrolyte include nitric acid, acetic acid, hydrochloric acid, lithium hydroxide, and potassium chloride, and among them, nitric acid is preferable because the effect on the analysis can be sufficiently avoided.

The concentration of the electrolyte in the liquid sample is not particularly limited.

The liquid sample may be, for example, a sample of a liquid itself, or a sample containing a solid. Examples of the sample include a sample derived from a biological body, a sample derived from environment, a metal, a chemical substance, and a pharmaceutical. The sample derived from a biological body is not particularly limited, and examples thereof include urine, blood, hair, and a umbilical cord. Examples of the blood sample include erythrocyte, whole blood, serum, and plasma. Examples of the biological body include humans, nonhuman animals, and plants. Examples of the nonhuman animals include mammals except for humans, and fish and seafood. A sample derived from the environment is not particularly limited, and examples thereof include food, water, the ground, the atmosphere, and air. Examples of metals include heavy metals such as Bi (bismuth), Hg (mercury), Cd (cadmium), Pd (palladium), Zn (zinc), Tl (thallium), Ag (silver), and Pb (lead). Examples of chemical substances include reagents, pesticides, and cosmetics. Examples of foods include fresh food and processed food. Examples of water include drinking water, ground water, river water, seawater, and domestic wastewater.

In the case where a subject to be analyzed is a metal, the liquid sample may contain a reagent for separating a metal in the sample, for example. The reagent can be, for example, a chelating reagent, an acid, or an alkali, and specific examples thereof include dithizone, thiopronine, meso-2,3-dimercapto succinic acid (DMSA), sodium hydroxide, lithium hydroxide, 1,2-dimercapto-1-propanesulfonic acid sodium salt (DMPS), nitric acid, succinic acid, glycine, and cysteine.

It is preferred that, in the plasma spectrometry method of the present invention, the cathode and the anode forming the electrode system is arranged so as to be partially or entirely in contact with the conductive solution. Moreover, it is preferred that the cathode is arranged on the upstream side of the narrow portion, and the anode is arranged on the downstream side of the narrow portion.

In the step of the voltage application, when an electric field is generated in a channel containing a conductive solution supplied therein by applying a voltage to an electrode system including a pair of electrodes, air bubbles are generated in the narrow portion, and plasma is generated in the generated air bubbles, for example.

A voltage can be applied to the electrode system using a voltage application unit. The voltage application unit is not particularly limited as long as a voltage can be applied between the electrodes, and a voltage generator or the like can be used as a known unit. A voltage to be applied between the electrodes is not particularly limited and can be set appropriately according to the sizes of air bubbles to be generated, the size and conditions of plasma to be generated, the kind of the conductive solution, the lengths and sizes of the channel and the narrow portion, and the like, for example. The voltage can be set from 30 to 5000 V, or from 100 to 1500 V, for example and the current between the electrodes can be set from 0.1 to 1000 mA, or from 2 to 100 mA, for example.

The intensity of the electric field in the channel is not particularly limited and can be set appropriately according to the kind of the conductive solution, the lengths and the sizes of the channel and the narrow portion, and the like, for example. The intensity of the electric field can be set from 0.01 to 100 MV/m, or from 1 to 10 MV/m, for example.

A voltage may be applied between electrodes continuously or discontinuously, for example. The time to apply a voltage is, for example, in the case of continuous application, from 1 to 1000 ms per one time. In the case of discontinuous application, the number of applications of voltage is, for example, from 1 to 1000 times, or from 10 to 50 times per 1 second, and the time to apply a voltage is, for example, from 1 µs to 500 ms, or from 20 µs to 5 ms per one time.

In the detection step, light emission caused by plasma generated in the channel in the step of the voltage application is detected. In the detection step, a region to be detected in the channel is not particularly limited and is as mentioned above, and for example, it is preferred that plasma light emission generated in the narrow portion is detected.

(4) Embodiments

The first embodiment of the present invention is described in detail with reference to drawings and examples. The present invention, however is not limited by the following examples. The identical parts in the drawings are denoted by identical reference numerals, and the first embodiment can be described with reference to the description of any of the other embodiments, unless otherwise shown. There is a case where the structure of each portion may be simplistically shown as appropriate in the drawings as a matter of convenience of the description, so that there is a case where the size, the proportion, and the like of each portion are different from the actual size, proportion, and the like, and the drawings are schematically shown.

Figure 1B:
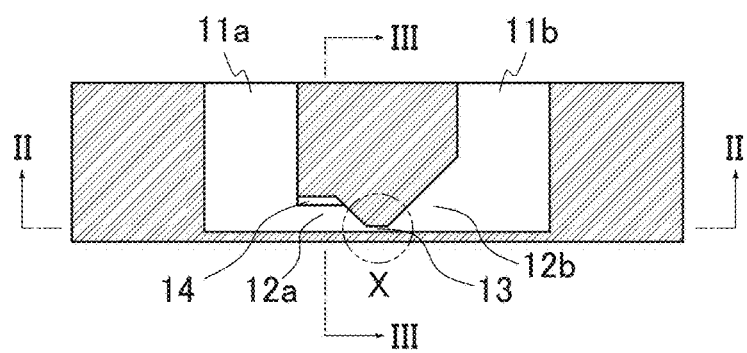
Figure 1C:
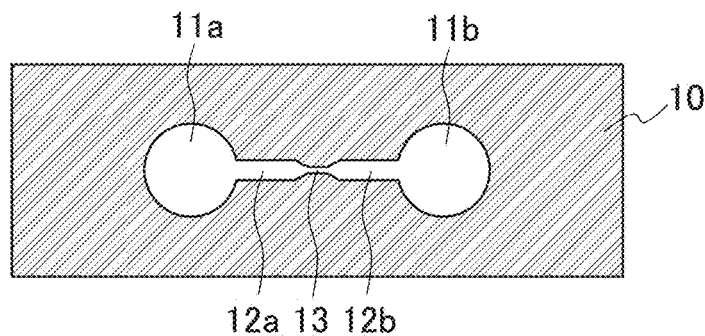
Figure 1D:
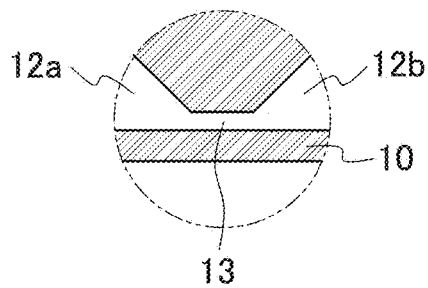
Figure 1E:
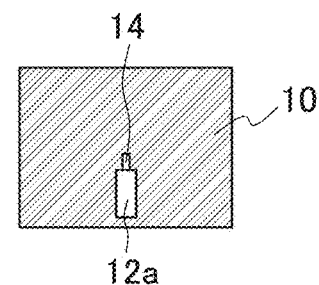

As an example of the first chip for plasma generation of the present invention, an embodiment in which a grooved portion is formed in a first region is shown in the schematic views of FIGS. 1A to 1E. FIG. 1A is a top view of a chip 101 for plasma generation. FIG. 1B is a cross-sectional view in the I-I direction of FIG. 1A. FIG. 1C is a cross-sectional view in the II-II direction of FIG. 1B. FIG. 1D is an enlarged view of a region (X) indicated by the dashed lines in FIG. 1B. FIG. 1E is a cross-sectional view in the III-III direction of FIG. 1B.

As shown in FIGS. 1A to 1E, the chip 101 for plasma generation includes a base material 10 including a channel, a first reservoir 11*a*, and a second reservoir 11*b* formed therein. In FIGS. 1A to 1E, the direction connecting between the first reservoir 11*a* and the second reservoir 11*b*, i.e., the lateral direction in FIG. 1A is the longitudinal direction of the chip 101, the first reservoir 11*a* side is the upstream side, and the second reservoir 11*b* side is the downstream side. In FIGS. 1A to 1E, the direction perpendicular to the longitudinal direction in the upper surface of the chip 101, i.e., the vertical direction in FIG. 1A is the width direction of the chip 101. In FIGS. 1A to 1E, the direction perpendicular to the longitudinal direction in the cross section of the chip 101, i.e., the vertical direction in FIG. 1B is the height direction of the chip 101. The base material 10 has, as a channel, in this order, a first region 12*a*, a narrow portion 13, and a second region 12*b* inside of which are in communication with one another, the end on the upstream side of the first region 12*a* is in communication with one end of the first reservoir 11*a*, and the end on the downstream side of the second region 12*b* is in communication with one end of the second reservoir 11*b*. Each of the first reservoir 11*a* and the second reservoir 11*b* is a concave portion having a cylindrical shape, provided in the height direction of the base material 10 and is opened to the upper surface of the base material 10.

The narrow portion 13 has a width narrower than the first region 12a and the second region 12b as shown in the plan views of FIGS. 1A to 1C and has a height lower than the first region 12a and the second region 12b as shown in the cross-sectional views in the longitudinal direction in FIGS. 1B and 1D. Thus, the narrow portion 13 has a cross-sectional area smaller than the first region 12a and the second region 12b.

Specifically, as shown in the plan views of FIGS. 1A to 1C, the narrow portion 13 maintains an almost constant width. As shown in the plan views of FIGS. 1A and 1C, the width of the first region 12a is enlarged from a connection position with the narrow portion 13 as a starting point toward the upstream side so as to have a tapered shape and is maintained to be constant from the position at which the width reaches a constant width toward the upstream side. Similarly, the width of the second region 12b also is enlarged from the connection position with the narrow portion 13 as a starting point toward the downstream side so as to have a tapered shape and is maintained to be constant from the position at which the width reaches a constant width toward the downstream side. Moreover, as shown in the cross-sectional view of FIG. 1B, the height of the narrow portion 13 is maintained to be an almost constant height. The first region 12a has a tapered portion in which the height is enlarged and a non-tapered portion in which the height is constant. Specifically, the height of the first region 12a is gradually increased by enlarging the upper surface of the first region 12a from a connection position with the narrow portion 13 as a starting point toward a predetermined position so as to have a tapered shape and is maintained to be constant from the predetermined position toward the connection position with the first reservoir 11a. Furthermore, in the first region 12a, the upper surface of the portion in which the height is maintained to be constant has a grooved portion 14 along the longitudinal direction. Moreover, the second region 12b has a tapered portion, and the height of the second region 12b is gradually increased by enlarging the upper surface of the second region 12b from the connection position with the narrow portion 13 as a starting point toward the connection position with the second reservoir 11b so as to have a tapered shape.

The angle of the tapered portion in the first region 12a can be any of the above-mentioned examples. The length of the tapered portion in the first region 12a is, for example, 0 µm or from more than 0 µm to 5000 µm, from more than 0 µm to 3000 µm, or from 300 to 1300 µm. The length of the non-tapered portion in the first region 12a is, for example, 0 µm or from more than 0 to 5 mm, from more than 0 µm to 4 mm, or from more than 0 µm to 3 mm. The height of the non-tapered portion is, for example, 0 mm or from more than 0 mm to 5 mm, from more than 0 mm to 1 mm, or from more than 0 mm to 0.8 mm.

The width of the grooved portion 14 is, for example, from more than 0 µm to 1000 µm, from more than 0 µm to 500 µm, or from more than 0 µm to 300 µm, and the depth of the grooved portion 14 is, for example, from more than 0 µm to 5000 µm, from more than 0 µm to 3000 µm, or from more than 0 µm to 1000 µm.

The chip 101 for plasma generation can be used by setting it in a plasma generator including a voltage application unit and a detection unit, for example. In this case, the plasma generator or the chip 101 for plasma generation may include an electrode system to which a voltage is applied. In the former case, a cathode and an anode in the plasma generator may be inserted into a position at which the chip 101 for plasma generation is applied. As a specific example, it is preferred that the tip of the cathode is inserted into, for example, a position on the upstream side of the narrow portion 13, preferably the first region 12a in the chip 101 for plasma generation, and the tip of the anode is inserted into, for example, a position on the downstream side of the narrow portion 13, preferably the second region 12b in the chip 101 for plasma generation.

Then, by applying a voltage to the electrode system by the voltage application unit in the plasma generator, an electric field is generated in the chip 101 for plasma generation, air bubbles are generated, and plasma is generated from the air bubbles. Then, the generated plasma light emission is detected by the detection unit in the plasma generator.

Figure 2:
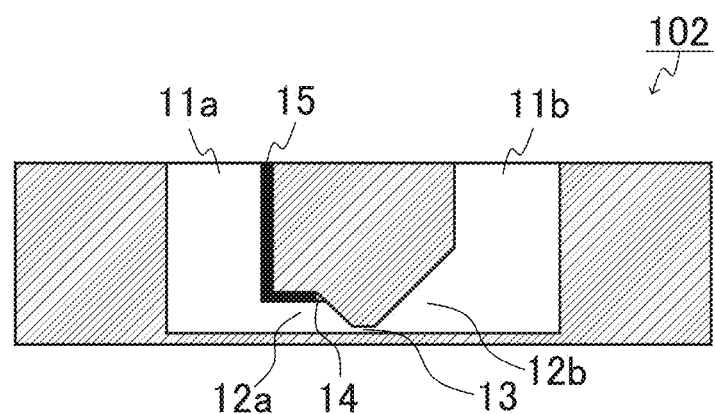
FIG. 2 is a cross-sectional view showing an example of the first chip for plasma generation according to the present invention.

Another example of the first chip for plasma generation of the present invention is shown in the schematic view of FIG. 2. FIG. 2 is a cross-sectional view in the same direction (I-I direction) as in FIG. 1B and is the same as FIG. 1B, unless otherwise shown.

As shown in FIG. 2, the chip 102 for plasma generation is an embodiment in which a cathode 15 is fixed to the inside (inner wall) of a grooved portion 14 in the first region 12a. Specifically, the cathode 15 is fixed from the inner wall of the grooved portion 14 in the first region 12a toward the inner wall of the first reservoir 11a so as to have a successive shape.

As to the cathode 15, the width is, for example, from more than 0 mm to 5 mm, from more than 0 mm to 3 mm, or from more than 0 mm to 1 mm, and the thickness is, for example, from more than 0 to 1000 µm, from more than 0 to 100 µm, or from more than 0 to 40 µm. The position of the tip of the cathode 15 is, for example, from the end on the downstream side of the first region 12a (end on the narrow portion 13 side), 0 mm or from more than 0 mm to 5 mm, or from more than 0 mm to 3 mm, or from more than 0 mm to 2 mm, or from more than 0 mm to 1 mm.

The chip 102 for plasma generation may further include an anode. It is preferred that the tip of the anode is arranged inside the second region 12b, more preferably fixed to the inner wall of the second region 12b, yet more preferably fixed from the second region 12b toward the inner wall of the second reservoir 11b so as to have a successive shape.

An example in which a grooved portion is formed in a first region is shown above as a specific example. The present invention, however, is not limited thereby, and as mentioned above, a grooved portion may be formed in a second region as a substitute for the first region, or grooved portions may be formed in both of the first region and the second region. The grooved portion of the second region can be described with reference to the description of the grooved portion in the first region by reading the first region as the second region, the upstream side as the downstream side, the downstream side as the upstream side, for example.

2. Second Embodiment of the Present Invention (1) Chip for Plasma Generation

As mentioned above, the second chip for plasma generation of the present invention includes a channel, the channel has a first region, a narrow portion, and a second region, the narrow portion is in communication with the first region and the second region and has a cross-sectional area smaller than the first region and the second region, and the chip satisfies at least one of the following conditions of (2): (2) the chip includes a cathode fixed to the inner wall of the first region.

In the chip for plasma generation of the present invention, high reproducibility of plasma light emission is achieved by fixing the cathode on the inner wall of the first region. In the conventional chip, solid electrodes such as bar electrodes are inserted into reservoirs are in communication with both ends of the channel, and a voltage is applied to generate plasma (Patent Literatures 1 to 3). However, the inventors of the present invention observed the finding that since a cathode and an anode are inserted into reservoirs at the both ends, a liquid resistance value between the electrodes varies, and the voltage to be applied to the channel becomes unstable when retention of air bubbles in the channel is generated. In contrast, in the chip for plasma generation of the present invention, the cathode is fixed to the inner wall of the first region, i.e., the cathode is fixed in a position near the narrow portion compared with the electrodes inserted into reservoirs. Therefore, for example, it is assumed that an influence of a change in resistance value in the entire channel is removed, the voltage to be applied between the electrodes is stabilized, and thus, the formation of the gas-liquid interface can be maintained to be constant. The present invention, however, is not limited by this assumption.

The chip for plasma generation of the present invention is characterized in that it satisfies the condition (2) as a substitute for the condition (1) in the above-mentioned first chip for plasma generation of the present invention and can be described with reference to the description of the first chip for plasma generation of the present invention except for the condition (2). The chip for plasma generation of the present invention may further satisfy the condition (1) in addition to the condition (2), for example.

The second chip for plasma generation of the present invention is characterized in that it includes a cathode, and the cathode is fixed to the inner wall of the first region and may or may not have a grooved portions in the inner walls of the first region and the second region in the first chip for plasma generation of the present invention.

(2) Plasma Generator

The second plasma generator of the present invention includes the second chip for plasma generation of the present invention as mentioned above. The second plasma generator of the present invention is characterized in that it includes the second chip for plasma generation, and the other configurations and conditions are not particularly limited. The second plasma generator of the present invention can be described with reference to the descriptions of the second chip for plasma generation of the present invention and the first embodiment of the present invention, unless otherwise shown.

It is preferred that the plasma generator of the present invention further includes a voltage application unit, a detection unit, and the like, for example.

(3) Plasma Spectrometry Method

As mentioned above, the second plasma spectrometry method of the present invention includes: an electric field generation step of generating an electric field in a channel containing a conductive solution supplied therein; and a detection step of detecting plasma light emission generated in the channel by the generation of the electric field, the channel has a first region, a narrow portion, and a second region, the narrow portion is in communication with the first region and the second region and has a cross-sectional area smaller than the first region and the second region, and the plasma spectrometry method satisfies the condition (2): (2) an anode and a cathode are arranged so that the narrow portion is positioned between the anode and the cathode, and the cathode is fixed to the inner wall of the first region.

In the plasma spectrometry method of the present invention, for example, the second chip for plasma generation or the second plasma generator of the present invention can be used. The plasma spectrometry method of the present invention can be described with reference to the descriptions of the second chip for plasma generation, the second plasma generator, and the first embodiment of the present invention, unless otherwise shown. It is preferred that the generation of the electric field is performed by applying a voltage to an electrode system, and in addition to this, for example, an electric field may be generated by microwave or the like, for example.

(4) Embodiment

The second embodiment of the present invention is described in detail with reference to the drawings and examples. The present invention, however, is not limited by the following examples. The identical parts in the drawings are denoted by identical reference numerals, and the second embodiment can be described with reference to the description of the first embodiment, unless otherwise shown. There is a case where the structure of each portion may be simplistically shown as appropriate in the drawings as a matter of convenience of the description, so that there is a case where the size, the proportion, and the like of each portion are different from the actual size, proportion, and the like, and the drawings are schematically shown.

Figure 3:
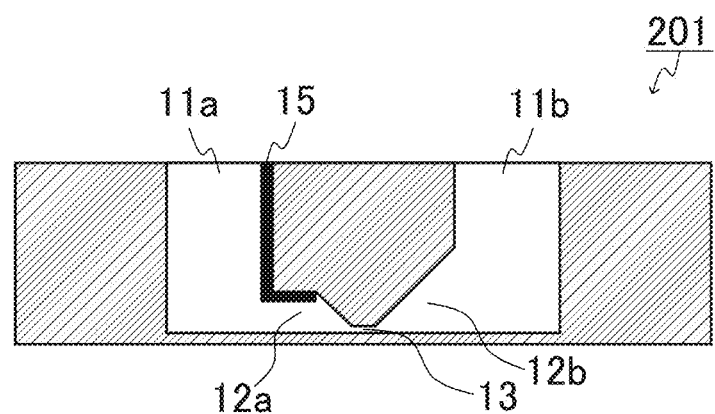
FIG. 3 is a cross-sectional view showing an example of the second chip for plasma generation according to the present invention.

An example of the second chip for plasma generation of the present invention is shown in the schematic view of FIG. 3. FIG. 3 is a cross-sectional view in the same direction (I-I direction) as in FIG. 1B. As shown in FIG. 3, a chip 201 for plasma generation is the same as the chip 102 for plasma generation in FIG. 2 except that a first region 12a does not have a grooved portion, and a cathode 15 is fixed to the inner wall of the first region 12a. Specifically, the first region 12a has a tapered portion and a non-tapered portion, and the height of the first region 12a is gradually increased by enlarging the upper surface of the first region 12a from a connection position with a narrow portion 13 toward a predetermined position so as to have a tapered shape and is maintained to be constant from the predetermined position toward a connection position with a first reservoir 11a. Then, the cathode 15 is fixed from the inner wall of the non-tapered portion in the first region 12a toward the inner wall of the first reservoir 11a so as to have a successive shape.

Figure 4:
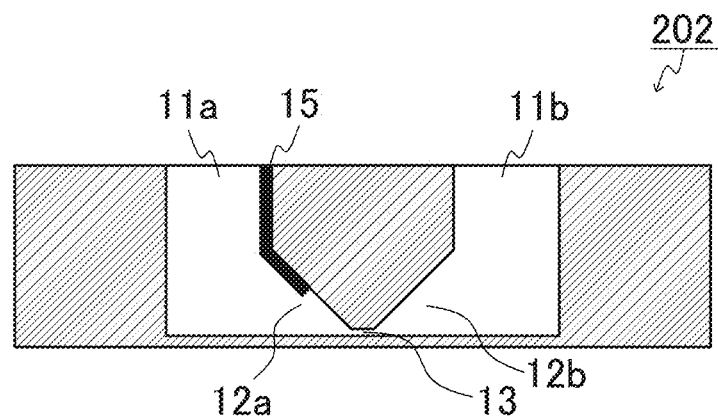
FIG. 4 is a cross-sectional view showing another example of the second chip for plasma generation according to the present invention.

Another example of the second chip for plasma generation of the present invention is shown in the schematic view of FIG. 4. FIG. 4 is a cross-sectional view in the same direction (I-I direction) as in FIG. 1B. As shown in FIG. 4, in the chip 202 for plasma generation, the first region 12a does not have a grooved portion, and the cathode 15 is fixed to the inner wall of the first region 12a. Specifically, the cathode 15 is fixed from the inner wall of the first region 12a toward the inner wall of the first reservoir 11a so as to have a successive shape.

Figure 5:
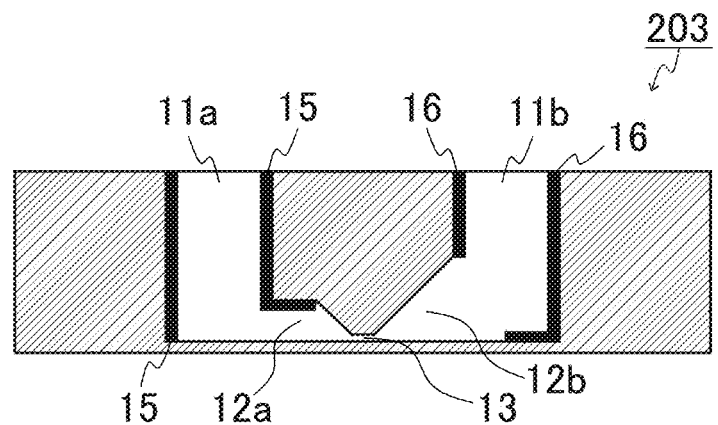
FIG. 5 is a cross-sectional view showing yet another example of the second chip for plasma generation according to the present invention.

Yet another example of the second chip for plasma generation of the present invention is shown in the schematic view of FIG. 5. FIG. 5 is a cross-sectional view in the same direction (I-I direction) as in FIG. 1B. As shown in FIG. 5, the chip 203 for plasma generation is the same as the chip 201 for plasma generation of FIG. 3 except that a cathode 15 is fixed to the inner walls of the first reservoir 11a and the first region 12a, and an anode 16 is fixed to the inner walls of the second reservoir 11b and the second region 12b.

The examples of the present invention are described below. The present invention, however, is not limited by the following examples.

EXAMPLES

Example 1A

The reproducibility of plasma light emission was determined using the first chip for plasma generation of the present invention.

(1) Chip for Plasma Generation

A chip 101 for plasma generation shown in FIGS. 1A to 1E was produced. Specifically, a plate of quartz glass as a lower substrate and a plate of polybutylene terephthalate (PBT, DURANEX®2002, manufactured by Polyplastic) as an upper surface were provided. A void shown in FIGS. 1A to 1E was formed in the upper substrate by a molding method, and the upper substrate and the lower substrate are then joined to each other with a ultraviolet curable adhesive. Thus, a chip 101 for plasma generation was produced.

The size of each portion of the chip 101 for plasma generation was set as follows.
Narrow portion 13
    Length: 600 μm
    Width: 220 μm
    Height: 30 μm
First region 12a
    Length: 2.5 mm
    Width: 1 mm
    Angle of tapered portion: 45°
Groove 14
    Length: 3 mm
    Width: 300 μm
    Depth: 1000 μm
Non-tapered portion
    Length: 2.2 mm
    Height: 2 mm
Second region 12b
    Length: 2.5 mm
    Width: 1 mm
    Angle of tapered portion: 45°
First reservoir 11a and Second reservoir 11b
    Diameter: 3.2 mm
    Height: 6 mm
Chip 101
    Full length: 35 mm
    Full width: 12 mm
    Height: 6 mm (2) Measurement of Plasma Light Emission Thiopronine was dissolved in nitric acid so as to have a final concentration of 500 mmol/L. Thus, a thiopronine sample was prepared. This was used as a conductive solution.

In the chip 101 for plasma generation, a cathode was inserted into a first reservoir 11a, and an anode was inserted into a second reservoir 11b. As the cathode and the anode, carbon electrode bars (DPP CRP microcarbon rod, diameter: 0.28 mm, manufactured by Sano Factory) were used. Subsequently, 80 μL of the conductive solution was introduced into the first reservoir of the chip 101 for plasma generation and was led out to the second reservoir 11b. Thus, the conductive solution was introduced into the first region 12a, the narrow portion 13, and the second region 12b.

Then, a voltage was applied between the cathode and the anode, and a light emission spectrum of plasma light emission in the narrow portion 13 of the chip 101 for plasma generation was analyzed. For the detection of light emission, a charge-coupled device (CCD) was used. The conditions under which a voltage was applied (hereinafter referred to as the application conditions) and the conditions under which plasma light emission was analyzed (hereinafter referred to as the analysis conditions) were as follows. The light exposure time is the time in which CCD for use in detection of light emission is on. Based on CCD-ON in which light emission is detected and CCD-OFF in which light emission is not detected as one cycle, the cycle was performed a total 160 cycles (times). While CCD-ON in one cycle, a close circuit (a voltage is applied) and an open circuit (a voltage is not applied) were repeated, and based on one time of close circuit and one time of open circuit as one set, the time in one set is referred to as the SW (switching) time, and the proportion (%) of the time of the close circuit in one set is referred to as Duty.

(Application Conditions)
Applied voltage: 750 V
Applied current: 750 mA
Application time: 350 ms
SW time: 50 μs
Duty: 16%
The number of applications: 160 times at intervals of 5000 ms (Analysis Conditions)
Analysis region: a region having a diameter of 400 μm with the center of the narrow portion as the central point
Optical fiber: a single core having a diameter of 400 μm
Spectroscope: VS-140-1G, manufactured by HORIBA, Ltd.

Figure 6:
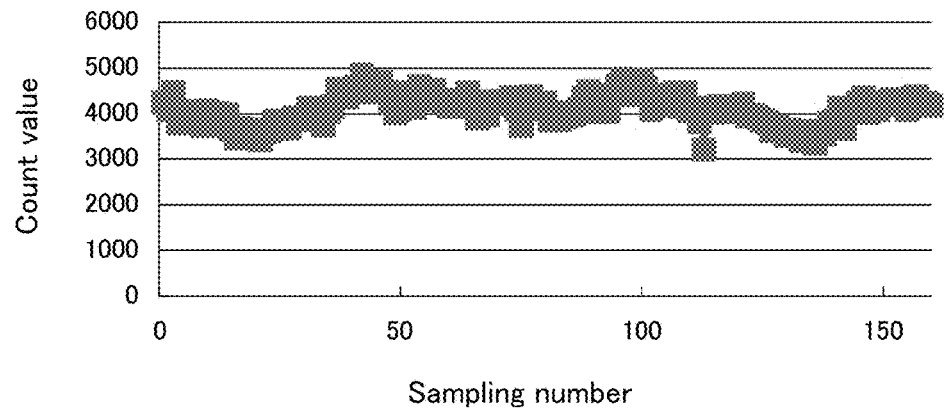
FIG. 6 is a graph showing the count value of plasma light emission and the sampling number in Example 1A of the present invention.

The application was performed a total of 160 times at intervals of 5000 ms, and the 160-time light emissions were analyzed. The results are shown in FIG. 6. FIG. 6 is a graph showing the count value of plasma light emission. In FIG. 6, the horizontal axis indicates the sampling number, and the vertical axis indicates the count value of plasma light emission.

As shown in FIG. 6, according to the chip 101 for plasma generation of the present example, the count number did not vary among the sampling numbers, and the coefficient of variation (C.V.) value of the count value at a wavelength of light emission spectrum of an element (mercury) of 253.97 nm was 8.2%. In each of the sampling numbers, a liquid resistance value between the electrodes was 18 kΩ which was not varied. Accordingly, the following was found. According to the first chip for plasma generation of the present invention, the change in liquid resistance value between electrodes is suppressed, and the voltage to be applied to a channel is stabilized. Thus, a high reproducibility of plasma light emission can be achieved.

Example 2A

The reproducibility of plasma light emission was determined using the second chip for plasma generation of the present invention.

(1) Chip for Plasma Generation

A chip 203 for plasma generation shown in FIG. 5 was produced. Specifically, a lower substrate and an upper substrate that are the same as those in Example 1A were provided, and a void shown in FIG. 5 was formed in the upper substrate in the same manner as described above. A cathode 15 and an anode 16 each having a thickness of 100 nm were formed in the inner wall of the upper substrate and the lower substrate by coating the inner walls with a gold using sputtering. Then, the upper substrate and the lower substrate were jointed to each other with an ultraviolet curable adhesive. Thus, a chip 203 for plasma generation was produced. In the chip 203 for plasma generation the cathode 15 is formed on the entire inner wall of the first reservoir 11a and the upper surface of the non-tapered portion of the first region 12a, and the anode was formed on the entire inner wall of the first reservoir 11a.

The size of each portion in the chip 203 for plasma generation was the same as in Example 1A.

(2) Measurement of Plasma Light Emission

A light emission spectrum of plasma light emission in the narrow portion was analyzed in the same manner as in Example 1A except that a voltage was applied between the cathode 15 and the anode 16 in the chip 203 for plasma generation a total of 40 times.

As a comparative example, plasma light emission was analyzed in the same manner as in Example 2A except that the cathode 15 and the anode 16 were not formed, and platinum electrode bars (Pt (wire), Φ: 0.5 mm, manufactured by Nilaco Corporation) as the cathode and the anode were inserted into the first reservoir 11a and the second reservoir 11b.

Figure 7:
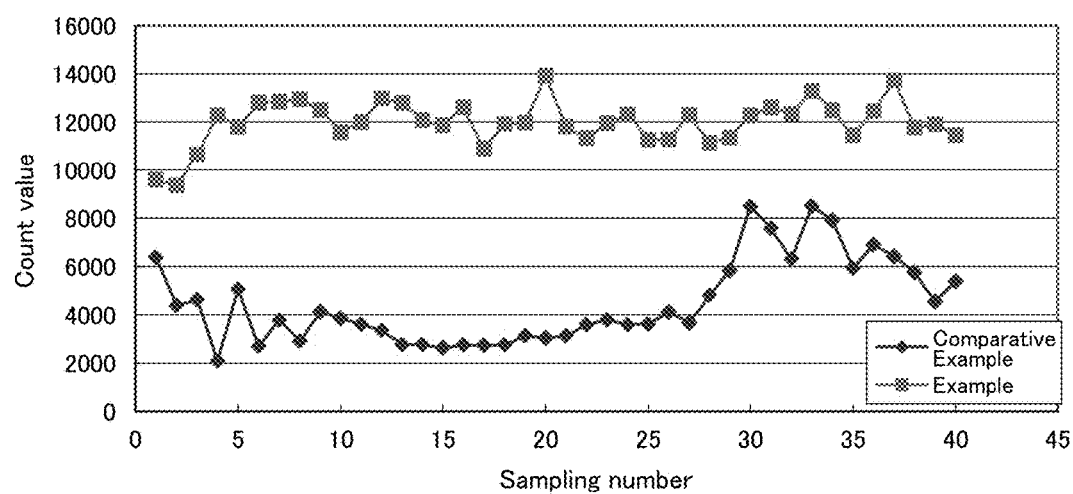
FIG. 7 is a graph showing the count value of plasma light emission and the sampling number in Example 2A of the present invention.
Figure 8:
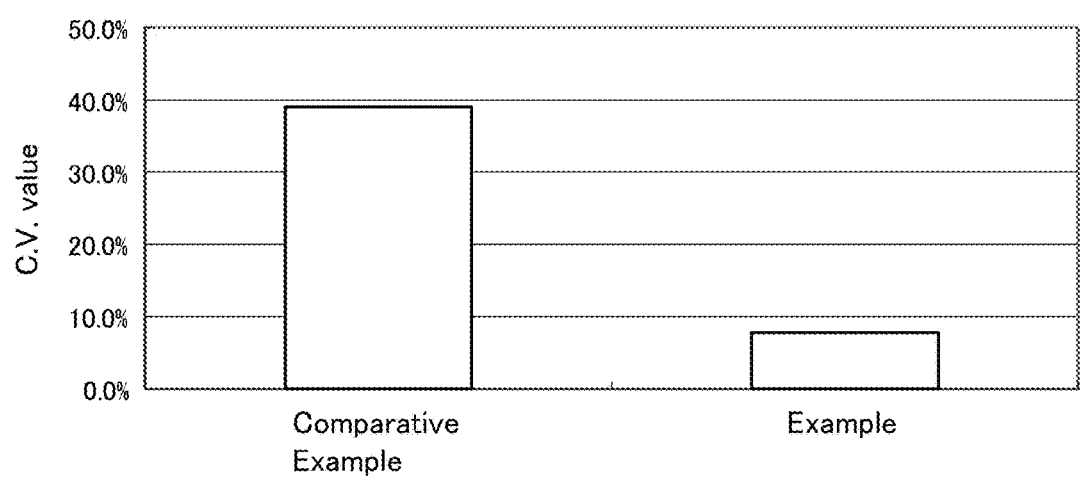
FIG. 8 is a graph showing the coefficient of variation (C.V.) value of the count value of plasma light emission in Example 2A of the present invention.

The results of these are shown in FIGS. 7 and 8. FIG. 7 is a graph showing the count value of plasma light emission, the horizontal axis indicates the sampling number, the vertical axis indicates the count value of plasma light emission, the square (■) shows the result of the present example, the rhombus (♦) shows the result of the comparative example. FIG. 8 is a graph showing the C.V. value of the count value of plasma light emission, the horizontal axis indicates the kind of sample, and the vertical axis indicates the C.V. value of the count value of plasma light emission.

As shown in FIG. 7, according to the chip 203 for plasma generation of the present example, the count value did not vary among the sampling numbers, and the count value of plasma light emission was high, compared with the chip for plasma generation of the comparative example. As shown in FIG. 8, according to the chip 203 for plasma generation of the present example, the C. V. value was reduced to $1/5$, compared with the chip for plasma generation of the comparative example. It can be said that this shows that the change in liquid resistance value between electrodes could be suppressed, and the voltage to be applied to a channel could be stabilized in the chip 203 for plasma generation of the present example. Thus, it was found that, according to the second chip for plasma generation of the present invention, the change in liquid resistance value between electrodes can be suppressed, and the voltage to be applied to a channel can be stabilized, and thus, high reproducibility of plasma light emission can be achieved.

While the present invention has been described with reference to exemplary embodiments and examples thereof, the present invention is not limited to these embodiments and examples. It will be understood by those of ordinary skill in the art that various changes in form and details may be made therein without departing from the scope of the present invention.

This application claims priority from Japanese Patent Application No. 2014-39506 filed on Feb. 28, 2014 and Japanese Patent Application No. 2015-33833 filed on Feb. 24, 2015, the entire subject matter of which are incorporated herein by reference.

INDUSTRIAL APPLICABILITY

According to the chip for plasma generation of the present invention, superior reproducibility of plasma light emission can be achieved without using a discharge unit for removing air bubbles, for example. Therefore, the present invention is really useful in analysis of element or the like utilizing plasma generation.

REFERENCE SIGNS LIST 10 substrate
11a first reservoir
11b second reservoir
12a first region
12b second region
13 narrow portion
14 grooved portion
15 cathode
101, 102, 201, 202, 203 chip for plasma generation

The invention claimed is:

1. A plasma generator comprising:
a chip for plasma generation, comprising:
a channel, wherein the channel has a first region, a narrow portion, and a second region, the narrow portion is in communication with the first region and the second region and has a cross-sectional area smaller than the first region and the second region, and the inner wall of the first region has a grooved portion with a longitudinal direction along the direction from the first region toward the second region;
a first reservoir and a second reservoir, for preserving a conductive solution, wherein one end of the first region is in communication with the narrow portion, and the other end of the first region is in communication with the first reservoir, and one end of the second region is in communication with the narrow portion, and the other end of the second region is in communication with the second reservoir;
a cathode, wherein the cathode is an electrode directly fixed to the inner walls of the first region and the first reservoir and directly fixed to the outer walls of the first region and the first reservoir;
an anode, wherein the anode is an electrode directly fixed to the inner walls of the second region and the second reservoir and directly fixed to the outer walls of the second region and the second reservoir;
a voltage application unit; and
a detection unit configured to detect plasma light emission generated in the chip.

2. The chip according to claim 1, wherein the cathode is arranged inside the grooved portion of the first region.

3. The chip according to claim 1, wherein the cathode is an electrode formed by coating the inner wall of the first region with a conductive material.

4. The chip according to claim 1, wherein the inner wall of the channel, having the cathode fixed thereon is the inner wall of the grooved portion in the channel.

5. The chip according to claim 1, wherein the cathode is an electrode formed by burying a conductive material in the inner wall of the first region.

6. The chip according to claim 5, wherein the inner wall of the channel, having the cathode fixed thereon is the inner wall of the grooved portion in the channel.

7. The chip according to claim 1,
wherein the anode is arranged on a side opposite to the cathode across the narrow portion.

8. The chip according to claim 7, wherein the anode is arranged inside the second region.

9. The chip according to claim 7, wherein the anode is fixed to the inner wall of the second region.

10. The chip according to claim 7, wherein the anode is an electrode formed by coating the inner wall of the second region with a conductive material.

11. The chip according to claim 7, wherein the anode is an electrode formed by burying a conductive material in the inner wall of the second region.

12. The plasma generator according to claim 1, wherein the plasma light emission is generated in the narrow portion of the channel in the chip.

13. A plasma spectrometry method comprising:
generating an electric field in a channel containing a conductive solution supplied therein; and
detecting plasma light emission generated in the channel by the generation of the electric field, wherein the channel has a first region, a narrow portion, and a second region, the narrow portion is in communication with the first region and the second region and has a cross-sectional area smaller than the first region and the second region, and
at least one of the inner walls of the first region and the second region has a grooved portion, and an anode and a cathode are arranged so that the narrow portion is positioned between the anode and the cathode, wherein the cathode is an electrode directly fixed to the inner walls of the first region and a first reservoir and directly fixed to the outer walls of the first region and a first reservoir, and the anode is an electrode directly fixed to the inner walls of the second region and a second reservoir and directly fixed to the outer walls of the second region and a second reservoir.

14. The plasma spectrometry method according to claim 13, wherein
in the detection step, plasma light emission is generated in the narrow portion.

\* \* \* \* \*